United States Patent [19]

Smith

[11] Patent Number: 4,576,949

[45] Date of Patent: Mar. 18, 1986

[54] USE OF 5,6,7,8-TETRAHYDROQUINOLINES AND 5,6-DIHYDROPYRINDINES AS LEUKOTRIENE AND LIPOXYGENASE INHIBITORS AND THE NOVEL 3-SUBSTITUTED COMPOUNDS THEREIN

[75] Inventor: Herman W. Smith, Kalamazoo, Mich.

[73] Assignee: The Upjohn Company, Kalamazoo, Mich.

[21] Appl. No.: 607,500

[22] Filed: May 7, 1984

[51] Int. Cl.$^4$ .................... A61K 31/41; C07D 221/20; C07D 215/54; C07D 215/20

[52] U.S. Cl. .................... 514/277; 514/299; 514/311; 514/312; 514/313; 546/14; 546/112; 546/152; 546/153; 546/155; 546/156; 546/168; 546/170; 546/174; 546/176; 546/15

[58] Field of Search .................... 546/14, 15, 112, 152, 546/153, 155, 156, 168, 170, 174, 176; 514/277, 299, 311, 312, 313

[56] References Cited

U.S. PATENT DOCUMENTS 2,868,691 1/1959 Porush et al. .................... 167/54
4,294,759 10/1981 Smith .................... 260/326.27

OTHER PUBLICATIONS

Samuelsson, Trends in Pharmacological Sciences, 5:227 (1980).
Samuelsson, et al., Annu. Rev. Biochem., 47:997–1029 (1978).
Samuelsson et al., Prostaglandins, 19:645 (1980).
D. J. Brien, et al., J. Chem. Soc. Chem. Commun., 1982, 133.
J. Epsztajn et al., Rocz. Chem., 1970, 44, 431 (CA72:132478h).
E. Reimann et al., Arch, Pharm., 1979, 312, 940.
Y. I. Chumakov, CA 77, 5306.
J. Epstajn et al., Bull. Acad. Pol. Sci., Ser. Sci. Chem., 1975, 23 917 (CA 85:46792t).
J. Epsztajn et al., Rocz. Chem., 1969, 43, 807 (CA 71:112773b).
W. Dammertz, E. Reimann, Arch. Pharm., 1980, 313, 826.
E. Reimann et al., Arch. Pharm., 1981, 314, 302.
U. Basu Ann. Chem., 530, 131 (1937), see CA 31, 3919 (1939).
E. Schroder et al., Eur. J. Med. Chem. (1979), 14, 309.
U.S. patent application Ser. No. 561,601.
P. E. Eaton et al., Synthesis, 1983, p. 796.
C. Ainsworth, Org. Syn., 1963, 4, p. 536.
R. Lukes, et al., Coll. Czech. Chem. Comm., 1960, 25, p. 607.
Maitle et al., Synthesis, 1981, p. 130.
J. Epsztajin et al., Rocz. Chem., 1975, 49, p. 123.
Bach, M. K. et al., A. New Inhibitor of Leukotriene C and D Synthesis: In Vitro Studies, Prostaglandins 23, 759–771, 1982.

*Primary Examiner*—Robert T. Bond
*Attorney, Agent, or Firm*—Martha A. Cox

[57] ABSTRACT

The present invention also provides novel compositions of matter. In particular, the present invention provides novel 3-substituted compounds of formula I which are from among the selected 5,6,7,8-tetrahydroquinolines and 5,6-dihydropyrindines having use as inhibitors of the synthesis of leukotrienes and as inhibitors of the action of lipoxygenase in mammalian metabolism.

18 Claims, No Drawings

4,576,949

USE OF 5,6,7,8-TETRAHYDROQUINOLINES AND 5,6-DIHYDROPYRINDINES AS LEUKOTRIENE AND LIPOXYGENASE INHIBITORS AND THE NOVEL 3-SUBSTITUTED COMPOUNDS THEREIN

DESCRIPTION

Background of the Invention

The present invention provides for the use of selected 5,6,7,8-tetrahydroquinolines and 5,6-dihydropyrindines as inhibitors of the synthesis of leukotrienes and as inhibitors of the action of lipoxygenase in mammalian metabolism.

The present invention also provides novel compositions of matter. In particular, the present invention provides novel 3-substituted compounds of formula I which are from among the selected 5,6,7,8-tetrahydroquinolines and 5,6-dihydropyrindines noted above having use as inhibitors of the synthesis of leukotrienes and as inhibitors of the action of lipoxygenase in mammalian metabolism.

The leukotrienes are a class of unsaturated fatty acid compounds which are derived from arachidonic acid by the action of lipoxygenase enzymes. See, e.g., Samuelsson, Trends in Pharmacological Sciences, 5:227 (1980); and Samuelsson, et al., Annu. Rev. Biochem., 47:997–1029 (1978). For a discussion of leukotriene nomenclature, see Samuelsson, et al., Prostaglandins, 19:645 (1980).

The utility of inhibitors of leukotriene biosynthesis and leukotriene antagonists and of inhibitors of the action of lipoxygenase includes treating or preventing pathological conditions associated with excessive or unbalanced production of leukotrienes and pathological conditions associated with lipoxygenase products. The treating or preventing of such pathological conditions by the inhibition of leukotrienes and action of lipoxygenase is known and includes use in treating or preventing allergy, and diseases of hypersensitivity and inflammatory origin. Therefore, more specifically the use of the selected 5,6,7,8-tetrahydroquinolines and 5,6-dihydropyrindines according to the present invention is for the therapeutic or prophylactic treatment of diseases, such as, allergy (reagin or non-reagin in nature), and especially asthma, chronic bronchitis, cystic fibrosis, psoriasis and in inflammatory bowel diseases.

INFORMATION DISCLOSURE

Certain 5,6,7,8-tetrahydroquinolines and 5,6-dihydropyrindines are known having the formula XXI, XXII, or XXIII as shown in the following TABLE I.

The references numbered 1 through 9 in TABLE I are:
1. D. J. Brien, A. Naiman, K. P. C. Vollhardt, J. Chem. Soc. Chem. Commun. 1982, 133.
2. J. Epsztajn et al., Rocz. Chem. 1970, 44, 431 (CA 72: 132478h).
3. E. Reimann et al., Arch. Pharm. 1979, 312, 940.
4. Y. I. Chumakov, CA 77, 5306.
5. J. Epsztajn et al., Bull. Acad. Pol. Sci., Ser. Sci. Chem. 1975, 23 917 (CA 85:46792t).
6. J. Epsztajn et al., Rocz. Chem. 1969, 43, 807 (CA 71:112773b).
7. W. Dammertz, E. Reimann, Arch. Pharm., 1980, 313, 826.
8. E. Reimann et al., Arch. Pharm. 1981, 314, 302.
9. U. Basu Ann. Chem. 530, 131 (1937); See CA 31, 3919 (1939).

No biological utilities are disclosed in the references of TABLE I.

On the other hand, Anti-inflammatory activity is disclosed by E. Schroder et al., Eur. J. Med. Chem. (1979), 14, 309, for 2-phenyl-5-carboxylic acid derivatives of tetrahydroquinoline and 5,6-dihydropyrindine. However, the 2-phenyl-5-carboxylic acid derivatives of Schroder et al. are different from The scope of the selected 5,6,7,8-tetrahydroquinolines and 5,6-dihydropyrindines of the present invention, which difference may be noted by both position and definition of substituents. Furthermore, an anti-inflammatory utility does not suggest inhibition of leukotriene synthesis or inhibition of the action of lipoxygenase of the present invention. Thus, the difference is outside of that made obvious to an ordinary artisan.

Copending U.S. patent applications disclosing activity dependent on inhibitions of leukotrienes and lipoxygenase product synthesis are found in U.S. application Ser. No. 159,738, issued as U.S. Pat. No. 4,294,759 for prostaglandin type compounds, U.S. application Ser. No. 561,601 for substituted naphthalenes, indoles, benzofurans, and benzothiophenes.

SUMMARY OF THE INVENTION

The present invention particularly provides:
a compound having the formula I
wherein
D is N or N→0;
wherein
n is an integer 0 or 1;
wherein
$R_1$ is
  (a) hydrogen
  (b) alkyl of from 1 to 4 carbons; inclusive,
  (c) cyclopropyl,

TABLE I

| Formula | $B_1$ | $B_2$ | $B_3$ | n | $B_4$ | References |
|---|---|---|---|---|---|---|
| XXI | $CH_3$ | $CO_2CH_2CH_3$ | H | 1 | — | 1 |
| XXI | $CH_3$ | $CO_2CH_2CH_3$ | H | 2 | — | 2 |
| XXI | $CH_3$ | H | H | 0,1 | — | 2 |
| XXI | H | H | $CH_3$ | 1 | — | 3 |
| XXI | H | $C_2H_5$ | H | 1 | — | 4 |
| XXI | $C_6H_5$ | H | H | 0,1,2 | — | 5 |
| XXII | $CH_3$ | H | H | 0,1 | 3-$NO_2$—$C_6H_4$, $C_6H_5$, | 6 |
| XXII | H | H | H | 1,2 | 3-$CH_3O$—$C_6H_4$ | 7 |
| XXII | H | H | $CH_3$ | 1 | $C_6H_5$ | 3 |
| XXIII | H | H | H | 2 | 3-$CH_3OC_6H_4$ | 7 |
| XXII | H | H | H | 1 | $C_6H_5$, | 8 |
| XXII | $CH_3$ | $CO_2CH_2CH_3$ | H | 0 | 3-$NO_2$—$C_6H_4$ | 9 |

(d) IX wherein a is an integer 0–2, inclusive, and wherein M is
  (i) hydrogen,
  (ii) halo,
  (iii) trifluoromethyl,
  (iv) S—CH$_3$,
  (v) phenyl,
  (vi) O—CH$_3$,
  (vii) OH,
  (viii) NO$_2$,
  (ix) NR$_3$R$_4$ wherein R$_3$ and R$_4$ are the same or different and are alkyl of from 1 to 4 carbons, inclusive, acyl, aroyl, hydrogen, or are taken together to form XI wherein q is an integer of 2 or 3, except that when one of R$_3$ or R$_4$ is acyl or aroyl, the other of R$_3$ or R$_4$ cannot be acyl or aroyl,
  (x) OCOCH$_3$,
  (xi) OCOC$_6$H$_5$,
  (xii) O—Si(CH$_3$)$_2$C(CH$_3$)$_3$; and
wherein
R$_2$ is
  (a) COOR$_5$ wherein R$_5$ is
    (i) hydrogen,
    (ii) alkyl of from one to four carbons, inclusive, or
    (iii) a pharmaceutically acceptable cation,
  (b) CH$_2$OH,
  (c) CHO,
  (d) CH=CH—(CH$_2$)$_d$R$_6$ comprising the cis or trans isomer thereof wherein d is an integer 0 through 3, and R$_6$ is CH$_2$OH, CH$_2$Cl, or CO$_2$R$_5$ wherein R$_5$ is as defined above,
  (e) CH$_2$CH$_2$(CH$_2$)$_d$R$_6$ wherein d and R$_6$ are as defined above; and
wherein
X is
  (a) XII, wherein M and a are as defined above except with the proviso that M cannot be NO$_2$ when D is N, R$_2$ is COOR$_5$ and n is 0,
  (b) XIII, wherein M and a are as defined above except with the proviso that M cannot be NO$_2$ when D is N, R$_2$ is COOR$_5$ and n is 0,
  (c) XIV,
  (d) XV,
  (e) CH—CH$_2$—C(O)—(CH$_2$)$_2$CH$_2$R$_7$ and R$_7$ is H, OH, Cl, XVI, or O—Si(CH$_3$)$_2$C(CH$_3$)$_3$,
  (f)  —CH—CH$_2$—C(OH)H—(CH$_2$)$_2$—CH$_2$R$_7$ wherein R$_7$ is as defined above, or
  (g) XVII wherein M and a are as defined above,
  (h) VIII;
and pharmaceutically acceptable salts thereof.

Additionally, the present invention provides for a method for the therapeutic or prophylactic treatment of diseases, such as, allergy, asthma, chronic bronchitis, cystic fibrosis, psoriasis, or inflammatory bowel disease comprising administration of an effective amount of a compound having the formula II
wherein
  D is N or N→0;
wherein
  n is an integer 0 or 1;
wherein
R$_8$ is
  (a) hydrogen,
  (b) alkyl of from 1 to 4 carbons; inclusive,
  (c) cyclopropyl, (d) IX wherein a is an integer 0–2, inclusive, and wherein M is
  (i) hydrogen,
  (ii) halo,
  (iii) trifluoromethyl,
  (iv) S—CH$_3$,
  (v) phenyl,
  (vi) O—CH$_3$,
  (vii) OH,
  (viii) NO$_2$,
  (ix) NR$_3$R$_4$ wherein R$_3$ and R$_4$ are the same or different and are alkyl of from 1 to 4 carbons, inclusive, acyl, aroyl, hydrogen, or are taken together to form XI wherein q is an integer 2 or 3, except that when one of R$_3$ and R$_4$ is acyl or aroyl, the other of R$_3$ and R$_4$ cannot be acyl or aroyl,
  (x) OCOCH$_3$,
  (xi) OCOC$_6$H$_5$,
  (xii) O—Si(CH$_3$)$_2$C(CH$_3$)$_3$; and
wherein
R$_9$ is
  (a) hydrogen, or alkyl of 1 to 4 carbon atoms,
  (b) COOR$_5$ wherein R$_5$ is
    (i) hydrogen,
    (ii) alkyl of from 1 to 4 carbons, inclusive, or
    (iii) a pharmaceutically acceptable cation,
  (c) CH$_2$OH,
  (d) CHO,
  (e) CH=CH—(CH$_2$)$_d$R$_6$ comprising the cis or trans isomer wherein d is an integer 0 through 3, inclusive, and R$_6$ is CH$_2$OH, CH$_2$Cl, or CO$_2$R$_5$ wherein R$_5$ is as defined above with the proviso that when R$_6$ is CO$_2$R$_5$ then d cannot be 0,
  (f) CH$_2$CH$_2$(CH$_2$)$_d$R$_6$ wherein d and R$_6$ are as defined above;
and
wherein
X is
  (a) XII wherein M and a are as defined above,
  (b) XIII wherein M and a are as defined above,
  (c) XIV,
  (d) XV,
  (e) CH—CH$_2$—C(O)—(CH$_2$)$_2$CH$_2$R$_7$ wherein R$_7$ is H, OH, Cl, XVI, or O—Si(CH$_3$)$_2$C(CH$_3$)$_3$,
  (f)  CH—CH$_2$—C(OH)H—(CH$_2$)$_2$—CH$_2$R$_7$ wherein R$_7$ is as defined above,
  (g) XVII wherein M and a are as defined above,
  (h) XVIII; with the proviso that when R$_8$ and R$_9$ are both hydrogen and n is 0 then X cannot be IX wherein M is hydrogen and with the proviso that when R$_8$ and R$_9$ are both hydrogen and n is 1 then M cannot be OC(=O) alkyl of from 1 to 4 carbons, inclusive, and
pharmaceutically acceptable salts thereof.

Examples of alkyl of from 1 to 4 carbons, inclusive, are methyl, ethyl, propyl, butyl, and isomeric forms thereof.

Halo means fluoro, chloro, bromo, and iodo.

Acyl means alkanoyl such as CH$_3$(CH$_2$)qC(O) having q an integer of 0 through 6, including isomer forms of CH$_3$(CH$_2$)$_q$—

Aroyl means substituents of formula VIII wherein M and a are defined above.

A pharmaceutically acceptable cation is such cations as Na, K, Li, ½ Ca, ½ Mg, ⅓ Al, ½ Fe, ⅓ Fe, NH$_4$, organic amines, such as long chain primary amines, e.g., decyl, lauryl, myristyl, palmityl, or stearyl amine, amines which yield crystalline salts with organic acid such as dicyclohexylamine, piperazine, benzylhydrylamine, amanatadine, or tris(hydroxymethyl aminomethane which can be produced by methods well known in the art. In compounds of formula I or II wherein $R_5$ is H or an ester group acid addition salts may be formed. Acids which form pharmacologically acceptable acid addition salts include hydrochloric, hydrobromic, hydroiodic, sulfuric, phosphoric, maleic, citric, tartaric, fumaric, acetic, and the like. Especially preferred among the pharmacologically acceptable acid addition salts within the scope of the present invention is hydrogen chloride.

As noted, the novel compounds and methods of using selected compounds of this invention have usefulness which results from inhibition of the formulation of leukotienes and lipoxygenase metabolites. Thus, tests for such inhibition show activity for such usefulness. Accordingly, the activity is effected by administration to mammals, including humans, whenever it is desirable medically to inhibit the production of leukotrienes and lipoxygenase metabolites.

Thus, the following TABLE II provides examples of the biological activity as determined by methods known in the art (see Bach, M. K., et al., 6,9-deepoxy-6,9-phenylimino-$\Delta$-6,8-prostaglandin $I_1$, (U-60,257). A New Inhibitor of Leukotriene C and D Synthesis: In Vitro Studies. Prostaglandins 23, 759–771, 1982.) for the present invention having formula II.

venous administration, and about 2 to 50 mg per kg of human body weight orally in single doses. The exact dose depends on the age, weight, and condition of the patient and on the frequency and route of administration. Such variations are within the skill of the practitioner or can be readily determined.

These compounds are effectively administered to human asthma patients by oral administration, aerosol administration or intravenously.

For administration by the oral inhalation route with conventional nebulizers or by oxygen aerosolization it is convenient to provide the instant active ingredient in dilute solution, preferably at concentrations of about 1 part of medicament to form about 100 to 200 parts by weight of total solution. Entirely conventional additives may be employed to stabilize these solutions or to provide isotonic media, for example, sodium chloride, sodium citrate, citric acid, sodium bisulfite, and the like can be employed.

For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Instead of a co-solvent there can also be used a dispensing agent such as oleyl alcohol. Suitable means to employ

TABLE II

| | | Compounds of Formula II | | | [a]LTC/LTD | | | |
|---|---|---|---|---|---|---|---|---|
| D | X | n | $R_8$ | $R_9$ | $IC_{50}$ | 0.1 | 1.0 | 10 μg |
| N | XII wherein M is p-acetoxy and a is 1 | 1 | $CH_3$ | $CO_2Et$ | | 89 | 78 | 34 |
| N | XII wherein M is H | 1 | $CH_3$ | $CO_2Et$ | | | 101 | 79 |
| N | XII wherein M is H | 1 | $CH_3$ | $CO_2Et$ | | | 96 | 44 |
| N | $CHCO(CH_2)_3OH$ | 1 | $CH_3$ | $CO_2Et$ | | 19 | 52 | 41 |
| N | XVII | 1 | $CH_3$ | $CO_2Et$ | 1.6 | | 46 | 1 |
| N | XIX | 1 | $CH_3$ | $CO_2Et$ | 6.7 | | 67 | 52 |
| N | XVII wherein M is p-methoxycarbonyl and a is 1 | 1 | $CH_3$ | $CO_2Et$ | | 26 | 49 | 22 |
| N | XVII wherein M is p-methoxycarbonyl and a is 1 | 1 | $CH_3$ | $CO_2Et$ | | 66 | 62 | 56 |
| N | XIV | 1 | $CH_3$ | $CO_2Et$ | | 94 | 66 | 16 |
| | | | | | | 120 | 113 | 31 |
| N | $CHCCH_2(CH_2)_2CH_3$ | 1 | $CH_3$ | $CO_2Et$ | | | 107 | 25 |
| | | | | | | | 76 | 63 |
| | | | | | | | 105 | 116 |
| N | $CH(CH_2)_3CH_2OH$ | 1 | $CH_3$ | $CO_2Et$ | | | 121 | 50 |
| | | | | | | | 140 | 190 |
| N | XII wherein M is H | 1 | $CH_3$ | $CH=CH-CO_2CH_3$ | | | 99 | 117 |
| N | XV | 1 | $CH_3$ | $CO_2Et$ | | | 122 | 41 |
| | | | | | | | 80 | 63 |
| N | XIII wherein M is H | 1 | $CH_3$ | $CO_2Et$ | | 110 | 54 | 12 |
| N | XIII wherein M is H | 1 | $CH_3$ | $CO_2Et$ | 6.8 | | 63 | 1 |
| | | | | | | | 30 | 0 |
| N | XII wherein M is H | 1 | H | H | 5.4 | | 105 | 33 |
| N | XV | 0 | H | H | 2.1 | | 67 | 15 |
| N | XII wherein M is p-acetoxy | 0 | H | H | | | 88 | 45 |

[a]Values for inhibition are expressed as % of control.
LTC/LTD is leukotriene C or D.

For the treatment described above the 5,6,7-tetrahydroquinoline or 5,6-dihydropyrindines are administered in a variety of dosage forms, for example, orally in the form of tablets, capsules, or liquids; rectally in the form of suppositories; parentally, subcutaneously, or intramuscularly; intravenously, as well as by intravenous infusion, topically, bucally, or by inhalation of an aerosol. The dosage is about 0.01 to 10 μg per kg per minute by intravenous infusion, is about 0.5 to 10 mg by intrathe aerosol inhalation therapy technique are described fully in U.S. Pat. No. 2,868,691, for example.

Certain compounds of the present invention are preferred. Thus, compounds of the formula I, wherein D is N, $R_2$ is $COOR_5$ and $CH_2CH_2(CH_2)_dR_6$ are preferred and the compound of formula I more preferred is the compound wherein D is N, $R_1$ is methyl, $R_2$ is ethoxycarbonyl and X is the formula XIII wherein M is hydrogen and the hydrogen chloride salt of the latter is the most preferred.

A process for preparing the novel compounds of formula I of the present invention is generally as shown in Schemes 1, 2, 3, 4, 5 and 6.

In Scheme 1 the 2-formyl-cyclopentanone of tautomeric formula A wherein n is 0 and 2-formylcyclohexanone of tautomeric formula A wherein n is 1 are prepared as described by P. E. Eaton, et al. *Synthesis* 1983, p. 796 and by C. Ainsworth, *Org. Syn.* 1963, 4, p. 536, respectively. Condensation of the compounds of formula A with the 3-amino-2-propenoates having the formula B, which compounds having formula B are prepared as described by R. Lukes, et al., *Coll. Czech. Chem. Comm.*, 1960, 25, p. 607 and P. Maitle et al., *Synthesis,* 1981, p. 130, is accomplished by a modification of the procedures published by J. Epsztajin et al., *Rocz. Chem.,* 1975, 49, and p. 123, and 1970, 44, p. 431. The modifications are those an ordinarily skilled artisan would understand for the variations required to make the novel compounds of the present invention. The condensation provides compounds having the formula C. An alternative process for the preparation of compounds of formula C wherein n is 1 and $R_1$ is methyl is reported by K. P. C. Vollhardt, *J. Chem. Soc. Chem. Commun.,* 1982, p. 133.

Novel compounds of the formula $I_2$ wherein n is 0 or n is 1, and wherein $X_2$ is the substituent XII, XIV or XV are shown as the product obtained in Scheme 2. The process of Scheme 2 condenses compounds of formula C wherein n is 0 or n is 1 (prepared in Scheme 1) with aldehydes of formula D. The conditions of the condensation in Scheme 2 are analogous to those reported by J. Epsztajn, et al., *Rocz. Chem.,* 1969, 43, p. 807 and by E. Reimann, et al., *Arch. Pharm.,* 1980, 313, p. 826 for unsubstituted and 2-substituted tetrahyroquinoline, pyridines, and cycloheptenopyridines. Reimann, et al. cited previously as No. 8 following Table I also discloses a process which generally provides the conditions for a catalytic reduction of the double bonds in compounds of formula $I_2$ wherein $X_2$ is XII to provide compounds of formula $I_3$ wherein $X_3$ is the substituent XIII. The reduction is as shown in Scheme 3.

In Scheme 4 processes to produce variations in the $R_2$ side chain of the present invention are shown to be obtained by treating the compound having formula C described above. These variations are accomplished by one of the following methods. For example, a compound having formula C is reduced to obtain a carbinol of the compound having formula E wherein $R_2$ is $CH_2OH$. The carbinol is oxidized with activated $MnO_2$ to a carboxaldehyde of the compound having formula E wherein $R_2$ is CHO. Homologs of the aldehyde are prepared by reacting the aldehyde in a Wittig reaction. The Wittig reaction provides compounds of formula E wherein $R_2$ is $CH=CH_2(CH_2)_dCO_2R_6$ wherein d is in a range of greater than 0 to 3. If homologs of the aldehyde having d equal to 0 are desired the aldehyde is subjected to the Doebner reaction. Both the Wittig and Doebner reaction are well known in the art.

The unsaturated homologs above may then be reduced by catalytic hydrogenation to produce compounds having formula E wherein $R_2$ is $CH_2CH_2(CH_2)_dR_6$.

The compounds of formula E may be treated consecutively as discussed above for Schemes 2 and 3 to obtain a desired corresponding substituent X as shown for compounds of formula $I_2$ and $I_3$. See Scheme 5 steps $Q_1$ and $Q_2$. Scheme 5 also shows that compounds of formula $I_3$ can be treated in a manner similar to that described for Scheme 4 to replace the $CO_2CH_2CH_3$ group with corresponding groups denoted $R_2$ and defined to include $CH_2OH$, CHO, $CH=CH-(CH_2)_dCO_2R_6$ or $CHCH_2(CH_2)_dCO_2R_6$. This latter treatment of formula $I_3$ is shown as $Q_3$ in Scheme 5.

Finally, Scheme 6 shows catalytic hydrogenation of compounds of formula $I_2$ prepared in Scheme 2 described above. The hydrogenation produces a product mixture from which compounds having formula $I_6$ are or can be prepared wherein $X_6$ is $C(=O)CH_2CH_2CH_2R_7$, $CHCH_2C(OH)HCH_2CH_2CH_2R_7$, XIV, XV.

The process for preparing the novel compound of the present invention is described more fully in the preparation and examples given below. These examples are not meant to be limiting and variations for processes to prepare compounds generally within the scope as defined for formula I above are within the skill of an ordinary artisan.

PREPARATION I 5,6,7,8-Tetrahydro-2-methyl-3-quinolinecarboxylic acid ethyl ester A solution of 2-formylcyclohexanone (19.0 g) and ethyl-3-aminocrotonate (19.4 g) in toluene (25 ml) is azeotropically distilled for 2.5 hours. The dark solution is diluted with ethyl acetate and 5,6,7,8-tetrahydro-2-methyl-3-quinolinecarboxylic acid ethyl ester is extracted into 2N hydrochloric acid. The acid extract is neutralized and the oil which precipitated is extracted into ether to yield crude 5-carboethoxy-2,3-cyclohexenopyridine (21.25 g). Purification of crude 5,6,7,8-tetrahydro-2-methyl-3-quinolinecarboxylic acid ethyl ester (29.7 g) on silica gel (500 g) with 4:1 Skelly B:ethyl acetate (200 ml) fractions gives pure 5,6,7,8-tetrahydro-2-methyl-3-quinolinecarboxylic acid ethyl ester (22.1 g) as a colorless oil. The hydrochloride salt of 5,6,7,8-tetrahydro-2-methyl-3-quinolinecarboxylic acid ethyl ester (m.p. 105° C.-106° C.) is obtained with ethereal hydrogen chloride and crystallized from ethyl acetate.

5,6,7,8-Tetrahydro-2-methyl-3-quinolinecarboxylic acid ethyl ester.

IR film 2960 (sh), 2920, 2850, 1715, 1595, 1550, 1425, 1400, 1360, 1305, 1285, 1230 (sh), 1150, 1055, 835, and 775 cm$^{-1}$.

NMR (CDCl$_3$)$\delta$1.39 (t, J=7 Hz, 3, CH$_3$), 1.87 (m, 4, CH$_2$), 2.65-3.05 (m, 7, CH$_2$, CH$_3$) 2.78 (S, CH$_3$), 4.40 (q, J=7 Hz, 2, CH$_2$), 7.94 (S, 1, ArH).

Hydrochloride salt of 5,6,7,8-tetrahydro-2-methyl-3-quinolinecarboxylic acid ethyl ester.

Anal. Calcd for: C, 61.05; H, 7.09; Cl, 13.86; N, 5.48. Found: C, 60.83; H, 6.96; Cl, 14.23; N, 5.38.

MS m/e 219 (M$^+$), 191, 190, 175, 174 (base peak), 173, 147, 146, 38 and 36.

EXAMPLE I

8-[[4-(Acetyloxy)phenyl]methylene]-5,6,7,8-tetrahydro-2-methyl-3-quinolinecarboxylic acid ethyl ester A solution of 5,6,7,8-tetrahydro-2-methyl-3-quinolinecarboxylic acid ethyl ester (2.19 g) and 4-hydroxybenzaldehyde (1.32 g, 11 mmol) in acetic anhydride (6.5 ml) is heated at reflux temperature for 18 hours. The solution is evaporated, the residue dissolved in tetrahydrofuran and crude 8-[[4-(acetyloxy)phenyl)- methylene]-5,6,7,8-tetrahydro-2-methyl-3-quinolinecarboxylic acid ethyl ester is precipitated with water to yield 3.4 g. Purification on silica gel (250 g) with 9:1 Skelly B:ethyl acetate gives pure 8-[[4-(acetyloxy)-phenyl)-methylene]-5,6,7,8-tetrahydro-2-methyl-3-quinolinecarboxylic acid ethyl ester (2.76 g), m.p. 112° C., after ethanol crystallization.

IR (mull) 1755, 1705, 1570, 1535, 1490, 1440, 1360, 1240, 1195, 1145, 1075, 1040, 1000 and 910 cm$^{-1}$.

NMR (CDCl$_3$) 1.37 (t, 3, CH$_3$), 1.55–2.05 (m, 2, CH$_2$), 2.25 (S, 3, CH$_3$), 2.5–3.0 (m, 7, CH$_2$, CH$_3$), 2.83 (S, CH$_3$), 4.36 (q, 2, CH$_2$), 7.0 (d, 2, ArH), 7.42 (d, 2, ArH), 7.90 (S, 1, CH), 8.12 (b, 1, CH).

MS m/e 365 (M+) 324, 323 (base peak), 322, 295, 294, 251, 250, and 43.

Anal. calcd for C$_{22}$H$_{23}$NO$_4$: C, 72.31, H, 6.34; N, 3.83. Found: C, 72.49; H, 6.40; N, 3.70.

UV (Ethanol) 231 (ε10,750), 279 (ε11,150) 334 (ε26,600) nm.

EXAMPLE II 5,6,7,8-Tetrahydro-2-methyl-8-(phenylmethylene)-3-quinolinecarboxylic acid ethyl ester A solution of 5,6,7,8-tetrahydro-2-methyl-3-quinolinecarboxylic acid ethyl ester (4.4 g) and benzaldehyde (2.54 g) in acetic anhydride (13 ml) is heated at reflux temperature for 5 hours. The residue from evaporation is dissolved in aqueous tetrahydrofuran, diluted with water, and the precipitate is extracted into ethyl acetate. The extract is washed with 5 percent sodium bicarbonate solution, dried and evaporated. The residue deposited pure 5,6,7,8-tetrahydro-2-methyl-8-(phenylmethylene)-3-quinolinecarboxylic acid ethyl ester (3.0 g, m.p. 125° C.–126° C.) from ethanol solution.

IR (mull) 1695, 1585, 1535, 1425, 1360, 1240, 1150, 1070, 1040 cm$^{-1}$.

NMR (CDCl$_3$) δ137 (t, 3, CH$_2$CH$_3$), 1.82 (m, 2, CH$_2$), 2.58–3.03 (m, 7, CH$_2$, CH$_3$), 2.82 (s, CH$_3$), 4.34 (q, 2, CH$_2$CH$_3$), 7.15–7.53 (m, 5, ArH), 7.90 (s, 1, ArH), 8.13 (s, 1, CH$_2$).

Ms m/e 307 (m+), 308, 306, 279, 278, 251, 235, 234, 91 and 29.

Anal. Calcd. for C$_{20}$H$_{21}$NO$_2$: C, 78.14; H, 6.98; N, 4.56. Found: C, 77.93; H, 6.95; N, 4.23.

EXAMPLE III 5,6,7,8-Tetrahydro-2-methyl-8-(phenylmethylene)-3-quinolinemethanol A suspension of LiAlH$_4$ (2.81 g) in THF (250 ml) is treated with 5,6,7,8-tetrahydro-2-methyl-8-(phenylmethylene)-3-quinolinecarboxylic acid ethyl ester (7.43 g) and reacted for 25 minutes. Excess reagent is quenched, the mixture is diluted with ethyl acetate and filtered. The filtrate is washed, dried and evaporated to yield crude 5,6,7,8-tetrahydro-2-methyl-8-(phenylmethylene)-3-quinolinemethanol (7.3 g). Crystallization from aqueous ethanol gives 5.10 g of pure 5,6,7,8-tetrahydro-2-methyl-8-(phenylmethylene)-3-quinolinemethanol (m.p. 102° C.–103° C.) as two crops.

IR (mull) 3400–3050, 1590, 1545, 1485, 1445, 1375, 1180, 1120, 1040, 990, 920, 760 and 700 cm$^{-1}$.

NMR (CDCl$_3$) δ1.5–2.05 (m, 2, CH$_2$), 2.33–3.15 (m, 8, OH, CH$_2$, CH$_3$), 2.50 (s, CH$_3$), 4.65 (s, 2, CH$_2$), 7.17–7.58 (m, 6, ArH), 7.27 (s, ArH), 7.97 (s, 1, CH=).

Ms m/e 265 (m+) 264, 248, 86, 59, 57, 56, 45, 43 and 42.

Anal. Calcd. for C$_{18}$N$_{19}$NO: C, 81.47; H, 7.22; N, 5.28. Found: C, 81.46; H, 7.30; N, 4.81.

EXAMPLE IV 5,6,7,8-Tetrahydro-2-methyl-8-(phenylmethylene)-3-quinolinecarboxaldehyde A solution of 5,6,7,8-tetrahydro-2-methyl-8-(phenylmethylene)-3-quinolinemethanol (5.3 g) in chloroform (150 ml) is treated with three portions (4.5 g) of activated manganese dioxide at 4 hour intervals during reflux reaction. The suspension is filtered and the filtrate is evaporated to yield crude 5,6,7,8-tetrahydro-2-methyl-8-(phenylmethylene)-3-quinolinecarboxaldehyde (5.3 g) as an oil. Filtration through silica gel (125 g) removes polar products and provides pure 5,6,7,8-tetrahydro-2-methyl-8-(phenylmethylene)-3-quinolinecarboxaldehyde (2.1 g). Activated MnO$_2$ (0.45 g) converts 5,6,7,8-tetrahydro-2-methyl-8-(phenylmethylene)-3-quinolinemethanol (0.15 g) to 5,6,7,8-tetrahydro-2-methyl-8-methyl(phenylmethylene)-3-quinolinecarboxaldehyde (m.p. 217°–219°) within 15 minutes in toluene (15 ml) under azeotropic distillation conditions.

IR (mull) 1695, 1575, 1525, 1485, 1430, 1290, 1205, 1105 and 750 cm$^{-1}$.

NMR (CDCl$_3$) δ1.82 (m, 2, CH$_2$), 2.78–3.15 (m, 7, CH$_2$, CH$_3$), 3.03 (s, CH$_3$), 7.27–7.60 (m, 5, ArH), 8.00 (s, 1, ArH), 8.39 (s, 1, =CH), 10.38, S, 1, CHO).

EXAMPLE V

3-[5,6,7,8-Tetrahydro-2-methyl-8-(phenylmethylene)-3-quinolinyl]-2-propenoic acid methyl ester A solution of 5,6,7,8-tetrahydro-2-methyl-8-(phenylmethylene)-3-quinolinecarboxaldehyde (0.80 g) in pyridine (20 ml) is treated with malonic acid (0.31 g) and heated at 75° C. for 4 hours. Additional malonic acid (1.25 g) is added and the reaction is continued for 24 hours. The residual acid obtained by solvent evaporation is esterified with excess ethereal diazomethane to provide crude ester (0.58 g).

Purification on silica gel (60 g) with 9:1 Skelly B:ethyl acetate (20 ml fractions) gives pure 3-[5,6,7,8-tetrahydro-2-methy-8-(phenylmethylene)-3-quinolinyl]-2-propenoic acid methyl ester (0.36 g), m.p. 121° C.–123° C. after hexane crystallization.

IR (mull) 1710, 1620, 1580, 1440, 1370, 1305, 1165, 965, and 760.

NMR (CDCl$_3$) δ1.74 (m, 2, CH$_2$), 2.56–3.0 (m, 7, CH$_2$, CH$_3$), 2.67 (s, C$_3$), 3.81 (s, 3, CH$_3$), 6.33 (d, J=16 Hz, 1CH=), 7.33 (m, 5, ArH), 7.51 (s, 1, CH=), 7.93 (d, J=16 Hz, 1 CH=), 8.07 (s, 1, ArH).

MS m/e 319 (m+), 318, 263, 262, 235, 234, 168, 119, 41 and 39.

Anal. Calcd. for C$_{21}$H$_{21}$NO$_2$: C, 78.97; H, 6.63; N, 4.39. Found: C, 78.87; H, 6.62; N, 3.84.

EXAMPLE VI 5,6,7,8-Tetrahydro-8-(phenylmethylene)-quinoline

A solution of 5-carboethoxy-2,3-cyclohexenopyridine (6.66 g) in acetic anhydride (20 ml) is treated with benzaldehyde (6.36 g) and heated at 120° C. for 96 hours. The dark solution is evaporated and the residue is purified on silica gel with Skelly B eluent. The eluted product (7.07 g) contains benzaldehyde and is crystallized from hexane to provide pure 5,6,7,8-tetrahydro-8-(phenylmethylene)quinoline (3.95 g), m.p. 58°–59° C.

IR (mull) 1575, 1555, 1435, 1175, 1110, 920, 885, 790, 770, 760, and 695 cm$^{-1}$.

NMR (CDCl$_3$), 1.78 (m, 2, CH$_2$), 2.80 (m, 4, CH$_2$), 6.97 (dd, J=3 Hz, J=9 Hz, 1, ArH), 7.1-7.5 (m, 6, ArH), 7.93 (s, 1, CH=), 6.40 (dd, 1, ArH).

MS m/e 221 (M+), 220 (base peak) 218, 217, 204, 109, 108, 102, and 97.

Anal. Calcd. for C$_{16}$H$_{15}$N: C, 86.84; H, 6.83; N, 6.33. Found: C, 87.10; H, 6.78; N, 6.29.

UV (ethanol) 222 ($\epsilon$9000), 269 ($\epsilon$15,200), 316 (68 18,900) nm.

EXAMPLE VII 6,7-Dihydro-7-(phenylmethylene)-5H-1-pyrinidine

A solution of 2,3-cyclopentenopyridine (5.95 g) in acetic anhydride (20 ml) is treated with benzaldehyde and is heated at reflux temperature for 96 hours. The solution is evaporated and the residue is dissolved in ethyl acetate, washed with 5 percent sodium bicarbonate solution, dried and evaporated. The residue of crude 6,7-dihydro-7-(phenylmethylene)-5H-1-pyrinidine is purified on silica gel (225 g) with 9:1 Skelly B:ethyl acetate to yield pure 6,7-dihydro-7-(phenylmethylene)-5H-1-pyrinidine (4.61 g), m.p. 74° C.-75° C. after hexane crystallization.

NMR (CDCl$_3$) $\delta$3.01 (s, 4, CH$_2$), 6.97 (dd, J=10/4 Hz, 1, ArH), 7.1-7.6 (m, 7, CH=, ArH), 7.84 (dd, 1, ArH).

MS m/e 207 (M+), 206, 205, 204, 178, 103, 102, 89 and 77.

Anal. Calcd. for C$_{15}$H$_{13}$N: C, 86.92; H, 6.32; N, 6.76. Found: C, 86.61; H, 6.25; N, 6.57.

UV (ethanol) 222 ($\epsilon$8550), 229 ($\epsilon$8600), 237 ($\epsilon$7150), 274 ($\epsilon$15750), 331 ($\epsilon$26258), and 342 sh ($\epsilon$22,750) nm.

EXAMPLE VIII

4-[(5,6-Dihydro-7H-pyrindin-7-ylidene)methyl]phenol acetate

A solution of 2,3-cyclopentenopyridine (11.9 g) in acetic anhydride (20 ml) is treated with 4-hydroxy benzaldehyde (12.2 g) and heated at reflux temperature for 6 days. The residue for evaporation of acetic anhydride is treated with 2N hydrochloric acid (100 ml) diluted to 500 ml and the mixture is extracted with ethyl acetate to remove neutral products. The aqueous phase is neutralized and the precipitated 4-[(5,6-dihydro-7H-pyrindin-7-ylidene)methyl]phenol acetate is extracted into ethyl acetate. Drying and evaporation of the extract gives crude 4-[(5,6-dihydro-7H-pyrindin-7-ylidene)methyl]-phenol acetate (14.41 g). Crystallization from methylene chloride solution provides pure 4-[(5,6-dihydro-7H-pyrindin-7-ylidene)methyl]phenol acetate (12.05 g), m.p. 125° C.-126° C.

IR (mull) 1755, 1690, 1670, 1495, 1415, 1280, 1200, 1165, 1050, 1015, 920, 855, 845, and 785 cm$^{-1}$.

NMR(CDCl$_3$) 67 2.27 (s, 3, CH$_3$), 3.01 (s, 4, CH$_2$), 7.03-7.30 (m, 3, ArH), 7.43-7.70 (m, 4, ArH, CH=), 8.50 (dd, J=2 Hz, 5 Hz, 1, ArH).

MS m/e 265 (M+), 264, 223, 222 (base peak), 221, 220, 194 and 192.

Anal. Calcd for C$_{17}$H$_{15}$NO$_2$: C, 76.92; H, 5.70; N, 5.28. Found: C, 76.61; H, 5.91; N, 5.17.

EXAMPLE IX

4-[(6,7-Dihydro-8-(5H)-quinolinylidene)methyl]-phenol acetate

A solution of 5-carboethoxy-2,3-cyclohexenopyridine as prepared in Preparation I (13.3 g) in acetic anhydride (20 ml) is treated with 4-hydroxybenzaldehyde and heated at reflux temperature for 5.5 hours. The solution is cooled and evaporated to a viscous residue. The residue is treated with 2N hydrochloric acid (75 ml) and neutral products removed by ethyl acetate extraction. The aqueous phase is neutralized and then the precipitated 4-[(6,7-dihydro-8-(5H)-quinolinylidene)methyl]-phenol acetate is extracted into ether. The ether extract is washed, dried and evaporated to yield crude 4-[(6,7-dihydro-8(5H)-quinolinylidene)methyl]-phenol acetate. Ethanol crystallization provides 10.80 g of pure 4-[(6,7-dihydro-8-(5H)-quinolinylidene)-methyl]-phenol acetate, m.p. 108° C.

IR (mull) 1755, 1590, 1565, 1505, 1440, 1425, 1385, 1225, 1210, 1190 (sh), 1175 (sh), 1120, 1020, 925, 910 (sh), 830, and 800 cm$^{-1}$.

NMR (CDCl$_3$) $\delta$1.82 (m, 2, CH$_2$), 2.28 (s, 3, CH$_3$), 2.87 (m, 4, CH$_2$), 6.8-7.2, (m, 3, ArH), 7.25-7.55 (m, 3, ArH), 7.97 (s, 1, CH=), 8.49 (dd, J=2 Hz, 5 Hz, 1, ArH).

MS m/e 279 (M+), 278, 237, 236 (base peak), 234, 220, 206, and 180.

Anal. Calcd. for C$_{18}$H$_{17}$NO$_2$: C, 77.39; H, 6.13; N, 5.01. Found: C, 77.15; H, 6.26; N, 5.12.

EXAMPLE X 5,6,7,8-Tetrahydro-2-methyl-3-quinolinecarboxylic acid

A solution of 5,6,7,8-tetrahydro-2-methyl-3-quinolinecarboxylic acid ethyl ester (1.6 g) in methanol (25 ml) is treated with N sodium hydroxide (8 ml) and heated at reflux temperature for 4 hours. The solution is concentrated, diluted with water and the solution is extracted with ethyl acetate. The washed extract is dried and evaporated to a viscous residue which crystallizes after trituration with ether. Recrystallization of the product (0.119 g) from methanol-ethyl acetate solution gives pure 5,6,7,8-tetrahydro-2-methyl-3-quinolinecarboxylic acid, m.p. 196° C.-197° C.

IR (film). 3100-2400, 2400-1800, 1700, 1550, 1445, 1265, 1145, 1040, 930 and 740 cm$^{-1}$.

MS m/e 191 (M+), 190, 163, 147, 146, 119, and 77.

Anal. Calcd for C$_{11}$H$_{13}$NO$_2$: C, 69.09; H, 6.85; N, 7.33. Found: C, 68.37; H, 6.74; N, 7.34.

EXAMPLE XI 8-(2-Furanylmethylene)-5,6,7,8-tetrahydro-2-methyl-3-quinolinecarboxylic acid ethyl ester A solution of 5,6,7,8-tetrahydro-2-methyl-3-quinolinecarboxylic acid (2.19 g) in acetic anhydride (10 ml) is treated with 2-furaldehyde (1.0 ml) and sodium acetate (0.82 g). The solution is treated at reflux temperature for 24 hours. The residue from the solvent evaporation is dissolved in ethyl acetate, washed with brine solution, dried and evaporated to a semi-crystalline residue (30 g). Filtration through silica gel (150 g) with 9:1 Skelly B:ethyl acetate gives 8-(2-furanylmethylene)-5,6,7,8-tetrahydro-2-methyl-3-quinolinecarboxylic acid ethyl ester (1.40 g), m.p. 119° C.–120° C. after hexane crystallization.

IR (mull) 1695, 1570, 1560, 1525, 1450, 1360, 1280, 1245, 1170, 1150, 1070, 1050, 1015, 930, 770 and 740 cm$^{-1}$.

NMR (CDCl$_3$) δ1.46 (t, 3, CH$_3$), 2.13 (m, 2, CH$_2$), 2.63–3.17 (m, 4, CH$_2$), 2.63 (s, 3, CH$_3$), 4.38 (q, 2, CH$_2$) 6.53 (s,2,ArH), 7.52 (s, 1, CH=), 7.95 (s, 2, ArH).

MS m/e 235 (M+), 218, 191, 190, 172, 146, 145, 144, 77 and 29.

Anal. Calcd. for C$_{18}$H$_{19}$NO$_3$: C, 72.70; H, 6.44; N, 4.71. Found: C, 72.37; H, 6.60; N, 4.30.

EXAMPLE XII 5,6,7,8-Tetrahydro-2-methyl-8-(2-thienylmethylene)-3-quinolinecarboxylic acid ethyl ester A solution of 5,6,7,8-tetrahydro-2-methyl-3-quinolinecarboxylic acid ethyl ester as prepared in Preparation I (3.66 g) in acetic anhydride (10 ml) is treated with sodium acetate (1.37 g) and 2-thiophenecarboxaldehyde (2.24 g). The solution is heated at reflux temperature for 56 hours. The cooled mixture is diluted with toluene, filtered and the filtrate evaporated to a solid residue. The residue is triturated with hexane and filtered to yield a residue of 5,6,7,8-tetrahydro-2-methyl-8-(2-thienylmethylene)-3-quinoline carboxylic acid ethyl ester (1.91 g) m.p. 117° C.–118° C. The filtrate residue is purified on silica gel (70 g) with 9:1 Skelly B:ethyl acetate as eluent. Fractions 7–13, 20 ml each, provide additional 5,6,7,8-tetrahydro-2-methyl-8-(2-thienylmethylene)-3-quinoline carboxylic acid ethyl ester (0.73 g). An analytical sample, m.p. 117° C.–118° C. is obtained by hexane recrystallization.

IR (mull) 1700, 1570, 1540, 1435, 1410, 1355, 1250, 1160, 1075, 1050, and 720 cm$^{-1}$.

NMR (CDCl$_3$) δ1.38 (t, 3, CH$_3$), 1.93 (m, 3, CH$_2$), 2.5–3.0 (m, 7, CH$_2$, CH$_3$), 2.83 (s, CH$_3$) 4.33 (q, 2, CH$_2$), 7.07 (m, 1, ArH), 7.30 (m, 2, ArH), 7.90 (s, 1, ArH), 8.30 (s, 1, CH=).

MS m/e 313 (M+), 312, 285, 284, 280, 268, 252, 238, and 97.

Anal. Calcd for: C$_{18}$H$_{19}$NO$_2$S: C, 68.97; H, 6.11; N, 4.47; S, 10.23. Found: C, 68.97; H, 6.17; N, 4.06; S, 10.34.

EXAMPLE XIII 5,7-Dihydro-7-(2-thienylmethylene)-5H-1-pyrindine

A solution of 2,3-cyclopentenopyridine (5.96 g) in acetic anhydride (20 ml) is treated with 2-thiophenecarboxaldehyde (6.06 g) and heated at gentle reflux temperature for 24 hours. Acetic anhydride is evaporated, the residue is digested with 5 percent sodium bicarbonate and the residual oil is extracted into ethyl acetate. Purification on silica gel (9:1 Skelly B:ethyl acetate) gives pure 5,7-dihydro-7-(2-thienylmethylene)-5H-1-pyrindine (2.85 g). Crystallization from hexane provides the analytical sample, m.p. 60° C.–61° C.

IR (mull) 1620, 1560, 1405, 1240, 1215, 1195, 1155, 1095, 880, 855, 820, and 780 cm$^{-1}$.

NMR (CDCl$_3$)δ 2.97 (s, 4, CH$_2$), 6.87–7.57 (m, 5, ArH), 7.73 (s, 1, CH=), 8.43 (d, J=5 Hz, 1, ArH$_4$).

MS m/e 213 (M+), 212 (base peak), 211, 210, 178, 167, 105, 69, and 32.

Anal. Calcd. for C$_{13}$H$_{11}$NS: C 73.20; H, 5.20; N, 6.57; S, 15.04. Found: C, 72.98; H, 5.19; N, 6.60; S, 14.56.

EXAMPLE XIV

3-[4-(Acetyloxy)phenyl]-6',7'-dihydro-2-methyl-spiro[oxirane-2,8'-(5'H)-quinoline]-3-carboxylic acid ethyl ester and the 1'-oxide thereof A solution of 8-[(4-acetyloxy)phenyl)methylene-5,6,7,8-tetrahydro-2-methyl-3-quinolinecarboxylic acid ethyl ester (0.61 g) in methylene chloride (10 ml) is treated with 3-chloroperoxybenzoic acid (0.86 g) and is reacted for 2 hours. The solution is diluted with ethyl acetate, washed with sodium thiosulfate and 5 percent sodium bicarbonate solution, dried, and evaporated to a viscous residue (1.34 g). Purification on silica gel (65 g) with 85:15 Skelly B:ethyl acetate gives 3-[4-(acetyloxy)phenyl]-6',7'-dihydro-2-methyl-spiro[oxirane-2,8'-(5'H)-quinoline]-3-carboxyic acid ethyl ester and the 1'-oxide thereof (0.31 g), m.p. 130° C. after ethyl acetate hexane crystallization. Continued elution with 1:1 ethyl acetate, Skelly B gives the 1'-oxide of 3-[4-(acetyloxy)phenyl]-6',7'-dihydro-2-methylspiro[oxirane-2,8'-(5'H)-quinoline]-3-carboxylic acid ethyl ester (0.17 g), m.p. 131° C.–132° C., after ether crystallization.

3-[4-(Acetyloxy)phenyl]-6',7'-dihydro-2-methyl-spiro[oxirane-2,8'-(5'H)-quinoline]-3-carboxylic acid ethyl ester.

IR (mull), 1745, 1710, 1590, 1545, 1500, 1265, 1200, 1180, 1140 (sh), 1115, 1060, 1005, 905, 875, and 850 cm$^{-1}$.

NMR CDCl$_3$ δ 1.38 (t, J=8 Hz, 3, CH$_3$), 1.81 (m, 4, CH$_2$), 2.27 (s, 3, CH$_3$), 2.7–2.95 (m, 5, CH$_2$), 2.80 (s, CH$_3$) 4.33 (q, 2, CH$_2$), 4.88 (s, 1, CH=O), 6.97 (d, 2, ArH), 7.87, (s, 1, ArH).

MS m/e 381 (M+) 352, 310, 308, 266, 233, 204, 161, and 107 (base peak).

Anal. Calcd for C$_{22}$H$_{23}$NO$_5$: C, 69.27; H, 6.08; N, 3.67. Found: C, 69.34; H, 6.00; N, 3.32.

U.V. (ethanol) 238 (ε 16,350), 288 (ε 12,200) nm.

1'-oxide of 3-[4-(acetyloxy)phenyl]-6',7'-dihydro-2-methyl-spiro[oxirane-2,8'-(5'H)-quinoline]-3-carboxylic acid ethyl ester IR (mull) 1745, 1710, 1500, 1300, 1235, 1205 (sh), 1180, 1075, 1045, 1010 (sh) and 900 cm$^{-1}$.

NMR (CDCl$_3$) δ 1.39 (t, 3, CH$_3$), 1.74 (m, 4 CH$_2$), 2.26 (s, 3, CH$_3$), 2.75–3.0 (m, 5, CH$_2$, CH$_3$), 2.72 (s, CH$_3$), 4.33 (q, 2, CH$_2$), 6.34 (s, 1, CH), 7.01 (d, J=9 Hz, 2, ArH), 7.35 (d, 2, ArH), 7.44 (s, 1, ArH).

MS m/e 397 (M+), 381, 380, 352, 310, 234, 233, 188, 179, 164, 121 (base peak).

Anal. Calcd for C$_{22}$H$_{23}$NO$_6$: C, 66.49, H, 5.83; N, 3.52. Found: C, 66.52, H, 5.85; N, 3.12.

U.V. (ethanol) 245 (ε 24,850), 274 (ε 7,700), 325 (ε 1,800) nm.

EXAMPLE XV 5,6,7,8-Tetrahydro-2-methyl-8-(2-oxopentyl)-3-quinolinecarboxylic acid ethyl ester IR (film) 1715, 1590, 1550, 1440, 1400, 1350, 1260, 1220 (sh), 1150, and 1050 cm$^{-1}$.

NMR (CDCl$_3$) δ 0.93 (t, 3, CH$_3$), 1.39 (t, 3, CH$_3$), 1.45–2.25 (m, 7, CH$_2$, CH$_3$), 2.70 (s, CH$_3$), 3.14 (dd, J=3 Hz, J=16 Hz, 1, CH$_2$), 3.40 (m, 1, CH), 4.33 (q, 2, CH$_2$), 7.83 (s, 1, ArH).

MS Calcd for C$_{18}$H$_{25}$NO$_3$: 303.1834. Found: 303.1816.

m/e 288, 260, 258, 232, 218.
Methoxime derivative:
Calcd for: $C_{19}H_{28}N_2O_3$. 332.2100. Found: 332.2099.

EXAMPLE XVI

5,6,7,8-Tetrahydro-8-(2-hydroxypentyl)-2-methyl-3-quinolinecarboxylic acid ethyl ester IR (film) 3200 (b), 1720, 1595, 1550, 1445, 1260, 1145, and 1155 cm$^{-1}$.

NMR (CDCl$_3$) δ 0.94 (t, 3, CH$_3$), 1.1–2.2 (m, CH$_2$, CH$_3$), 1.39 (t, CH$_3$), 2.5–3.2 (m, 5–6, CH$_3$, CH$_2$), 3.82 (m, 1, CH), 4.33 (q, 2, CH$_2$), 7.95 (s, 1, ArH).

MS TMS derivative: Calcd for: $C_{21}H_{35}NO_3Si$: C, 377.2886. Found: 377.2362.

m/e 362, 334, 332, and 232.

EXAMPLE XVII

5,6,7,8-Tetrahydro-8-(5-hydroxypentyl)-2-methyl-3-quinolinecarboxylic acid ethyl ester IR (film) 3300 (b), 1720, 1590, 1545, 1435, 1260, 1225 (sh), 1140, 1050, 900, and 720 cm$^{-1}$.

NMR (CDCl$_3$) δ 1.0–2.2, (m, CH$_2$, CH$_3$), 2.5–2.9, (m, 6, CH$_3$, CH$_2$), 2.73 (s, CH$_3$), 362 (t, 2, CH$_2$), 4.33 (q, 2, CH$_2$), 7.84 (s, 1, ArH).

MS. TMS derivative: Calcd for $C_{21}H_{35}NO_3Si$: 377.2386. Found: 377.2366.

EXAMPLE XVIII

5,6,7,8-Tetrahydro-2-methyl-8-(phenylmethyl)-3-quinolinecarboxylic acid ethyl ester and monohydrochloride A solution of 5,6,7,8-tetrahydro-2-methyl-8-(phenylmethylene)-3-quinolinecarboxylic acid ethyl ester (3.4 g) in ethyl acetate (150 ml) is treated with 10 percent palladium on carbon (0.70 g) and reduced at 40 p.s.i. hydrogen pressure for 3 hours. Catalyst is filtered and the filtrate is evaporated to yield 5,6,7,8-tetrahydro-2-methyl-8-(phenylmethyl)-3-quinolinecarboxylic acid ethyl ester (3.28 g) as an oil.

A solution of 5,6,7,8-tetrahydro-2-methyl-8-(phenylmethyl)-3-quinolinecarboxylic acid ethyl ester (3.4 g) in ether is treated at 0° with ethereal hydrogen chloride and the precipitated salt filtered to provide 3.4 g of the hydrochloride salt of 5,6,7,8-tetrahydro-2-methyl-8-(phenylmethyl)-3-quinolinecarboxylic acid ethyl ester. Crystallization from 2-propanol gives the pure hydrochloride salt of 5,6,7,8-tetrahydro-2-methyl-8-(phenylmethyl)-3-quinoline-carboxylic acid ethyl ester (3.15 g), m.p. 209° C.–210° C.

5,6,7,8-Tetrahydro-2-methyl-8-(phenylmethyl)-3-quinolinecarboxylic acid ethyl ester IR (film) 3000, 2975, 2925, 2850, 1730, 1600, 1560, 1500, 1450, 1275, 1240, 1160, 1070, 790, 760, and 700 cm$^{-1}$.

NMR (CDCl$_3$) δ 1.36 (t, 3, CH$_3$), 1.45–1.92 (m, 4, CH$_2$), 2.45–2.87 (m, 6, CH$_2$, CH$_3$), 2.83, (s, 3, CH$_3$), 2.93–3.33 (m, 1, CH), 3.59 (dd, J=3 Hz, 12 Hz, 1, CH$_2$), 4.39 (q, 2, CH$_2$), 7.33 (m, 5, ArH), 7.97 (S, 1, ArH).

MS m/e 309 (M+), 310, 308, 281, 280, 266, 218, 204, 190, 144.

The hydrochloride salt of 5,6,7,8-tetrahydro-2-methyl-8-(phenylmethyl)-3-quinolinecarboxylic acid ethyl ester.

Anal. Calcd for $C_{20}H_{23}NO_2HCl$: C, 69.45; H, 6.99; Cl, 10.25. Found: C, 69.06; H, 7.12; Cl, 10.20; N, 3.89.

IR (mull) 2500–2100, 2050, 1970, 1730, 1640, 1600, 1565, 1500, 1460, 1380, 1290, 1280, 1255, 1190, 1100, 1080, 985, 790, 740, and 700 cm$^{-1}$.

NMR (CDCl$_3$) δ 1.43 (t, 3, CH$_3$), 1.59–2.15 (m, 4, CH$_2$), 2.67 (t, J=12 Hz, 1, CH$_2$), 2.97 (m, 2, CH$_2$), 3.30 (s, 3, CH$_3$), 3.73 (dd, J=3 Hz, 12 Hz, 1, CH$_2$), 4.00–4.30 (m, 1, CH), 4.47 (q, 2, CH$_2$), 7.33 (m, 3, ArH), 7.60 (m, 2, ArH), 8.57 (s, 1, ArH).

EXAMPLE XIX

5,6,7,8-Tetrahydro-8-(5-hydroxy-2-oxopentyl)-2-methyl-3-quinolinecarboxylic acid ethyl ester as an oil.

IR (film) 3350, 1705, 1595, 1540, 1430, 1400, 1350, 1250, 1220 (sh), 1140, 1045 and 730 cm$^{-1}$.

NMR (CDCl$_3$) δ 1.36 (t, 3, CH$_3$), 1.5–2.5 (m, 10, CH$_2$), 2.55–2.90 (m, 5, CH$_2$, CH$_3$), 2.73 (s, CH$_3$), 3.43 (m, 1, CH), 3.67 (t, J=6 Hz, 2, CH$_2$) 4.33 (q, 2, CH$_2$), 7.82 (s, 1, ArH).

M.S. (TMS, Methoxime) Calcd for $C_{22}H_{36}N_2O_4Si$. 420.2444. Found: 420.2443.

EXAMPLE XX

8-(2-Furanylmethyl)-5,6,7,8-tetrahydro-2-methyl-3-quinolinecarboxylic acid ethyl ester as an oil IR (film) 1710, 1600, 1540, 1435, 1255, 1220, 1140, 1050, 995, 920, 770 and 715 cm$^{-1}$.

NMR (CDCl$_3$) δ 1.39 (t, 3, CH$_3$), 1.79 (m, 4, CH$_2$), 2.5–3.0 (m, 6, CH$_2$, CH$_3$), 2.78 (s, CH$_3$), 3.19 (m, 1, CH), 3.49 (dd, J=3 Hz, J=12 Hz, 1, CH$_2$—), 3.43 (q, 2, CH$_2$), 5.94 (d, 1, CH═), 6.23 (t, 1, CH═), 7.30 (1, CH═), 7.85 (s, 1, ArH$_4$).

MS m/e 299 (M+), 271, 270, 242, 219, 218, 190 and 81.

EXAMPLE XXI

5,6,7,8-Tetrahydro-2-methyl-8-[(tetrahydro-2-furanyl)methyl]-3-quinolinecarboxylic acid ethyl ester as an oil IR (film) 1710, 1595, 1545, 1440, 1400 (sh) 1360, 1250, 1220, 1140, 1050, 910, 770, 740 and 710 cm$^{-1}$.

NMR (CDCl$_3$) δ 1.39 (t, 3, CH$_3$), 1.5–2.4 (m, 10–11, CH$_2$), 2.4–3.2 (m, 6, CH$_2$, CH$_3$), 2.78 (s, CH$_3$), 3.55–4.2 (m, 3, CH, CH$_2$), 4.33 (q, 2, CH$_2$), 7.84 (s, 1, ArH).

MS m/e 303 (M+) 258, 220, 219 (base peak), 218, 204, 191, 190 and 43.

FORMULA

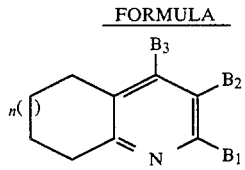

XXI

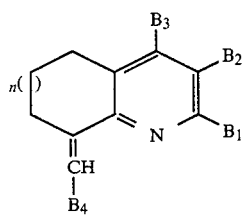

XXII

| FORMULA | |
|---|---|
| -continued structure with n(), N, CH₂B₄ | XXIII |
| Structure with n(), X, D, R₁, R₂ | I |
| Structure with n(), X, D, R₈, R₉ | II |
| Aryl ketone with Ma | VIII |
| Aryl with Ma | IX |
| (CH₂)_q ring | XI |
| C≡CH–aryl–Ma | XII |
| CH–CH₂–aryl–Ma | XIII |
| C≡CH–furan | XIV |
| C≡CH–thiophene | XV |
| Tetrahydropyran | XVI |
| Epoxide–aryl–Ma | XVII |
| CH–CH₂–furan | XVIII |
| CH–CH₂–tetrahydrofuran | XIX |

SCHEME 1

A: cyclohexanone-2-carboxaldehyde tautomers

B: H₂N–C(R₁)=CHCO₂CH₂CH₃

C: tetrahydroquinoline with CO₂CH₂CH₃ and R₁

SCHEME 2

C: tetrahydroquinoline intermediate

D: aryl-CHO (with Ma), furan-CHO, or thiophene-CHO

I₂: bicyclic product with X₂, N, R₁, CO₂CH₂CH₃

SCHEME 3

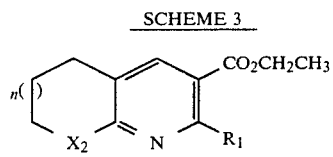

↓ H₂

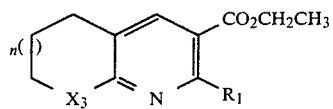

SCHEME 4

C

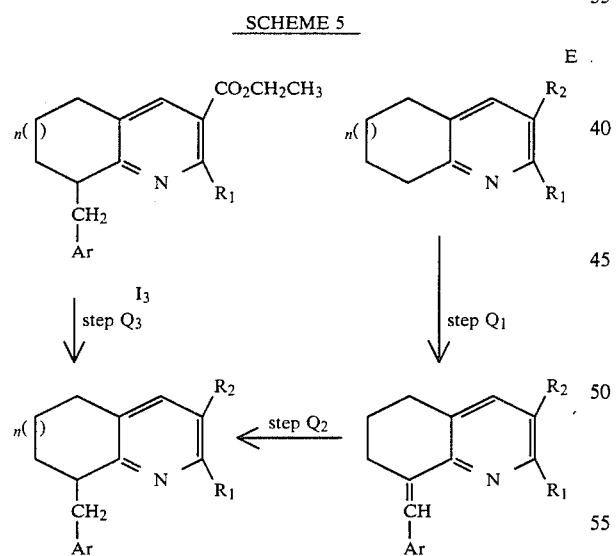

SCHEME 6

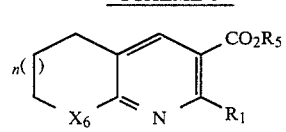

-continued
SCHEME 6

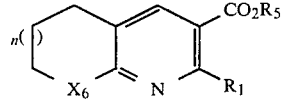

I claim:
1. A compound having the formula

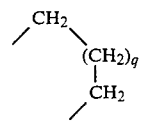

I wherein
D is N or N→O;
wherein
n is an integer 0 or 1;
wherein
$R_1$ is
(a) hydrogen,
(b) alkyl of from 1 to 4 carbons; inclusive,
(c) cyclopropyl, $$\text{(d)} - \underset{\text{Ma}}{\bigcirc}$$  IX wherein a is an integer 0-2, inclusive, and wherein M is
(i) hydrogen,
(ii) halo,
(iii) trifluoromethyl,
(iv) S—CH₃,
(v) phenyl,
(vi) O—CH₃,
(vii) OH,
(viii) NO₂,
(ix) NR₃R₄ wherein $R_3$ and $R_4$ are the same or different and are alkyl of from 1 to 4 carbons, inclusive, acyl, aroyl, hydrogen, or are taken together to form $$\begin{array}{c} \diagdown \text{CH}_2 \\ \phantom{xx}(\text{CH}_2)_q \\ \diagup \text{CH}_2 \end{array}$$  XI wherein q is an integer 2 or 3, except that when one of $R_3$ or $R_4$ is acyl or aroyl, the other of $R_3$ or $R_4$ cannot be acyl or aroyl,
(x) OCOCH₃,
(xi) OCOC₆H₅,
(xii) O—Si(CH₃)₂C(CH₃)₃; and
wherein
$R_2$ is
(a) COOR₅ wherein $R_5$ is
(i) hydrogen,
(ii) alkyl of from one to four carbons, or
(iii) a pharmaceutically acceptable cation,
(b) CH₂OH,
(c) CHO, (d) CH=CH—(CH$_2$)$_d$R$_6$ comprising the cis or trans isomer thereof wherein d is an integer 0 through 3, inclusive, and R$_6$ is CH$_2$OH, CH$_2$Cl or CO$_2$R$_5$ wherein R$_5$ is as defined above, (e) CH$_2$CH$_2$(CH$_2$)$_d$R$_6$ wherein d and R$_6$ are as defined above; and wherein
X is

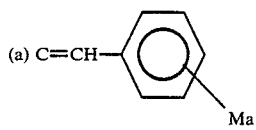   XII wherein M and a are as defined above except with the proviso that M cannot be NO$_2$ when D is N, R$_2$ is COOR$_5$ and n is 1,

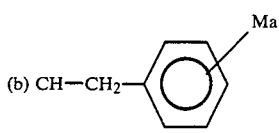   XIII wherein M and a are as defined above except with the proviso that M cannot be NO$_2$ when D is N, R$_2$ is COOR$_5$ and n is 1,

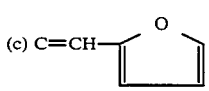   XIV

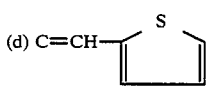   XV (e) CH—CH$_2$—C(O)—(CH$_2$)$_3$R$_7$ and R$_7$ is H, OH, Cl,

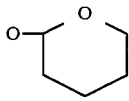   XVI or O—Si(CH$_3$)$_2$C(CH$_3$)$_3$,

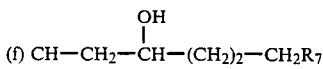

(f) CH—CH$_2$—CH(OH)—(CH$_2$)$_2$—CH$_2$R$_7$ wherein R$_7$ is as defined above, or

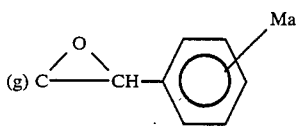   XVII wherein M and a are as defined above;

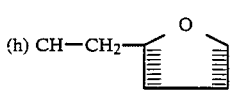   XVIII/XIX and pharmaceutically acceptable salts thereof.

2. A compound according to claim 1 wherein D is N.

3. A compound according to claim 2 wherein R$_2$ is CHO.

4. A compound according to claim 3 wherein R$_1$ is CH$_3$ and X is

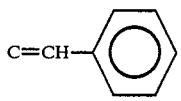   XII so that the embodiment is 5,6,7,8-tetrahydro-2-methyl-8-(phenylmethylene)-3-quinolinecarboxaldehyde.

5. A compound according to claim 2 wherein X is

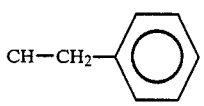   XIII

R$_1$ is CH$_3$, R$_2$ is CO$_2$CH$_2$CH$_3$, and n is 1 so that the specific embodiment is 5,6,7,8-tetrahydro-2-methyl-8-(phenylmethyl)-3-quinolinecarboxylic acid ethyl ester.

6. A compound according to claim 5 wherein the compound is the hydrogen chloride salt thereof.

7. A compound according to claim 2 wherein the specific embodiment is

8-[[4-(acetyloxy)phenyl]methylene]-5,6,7,8-tetrahydro-2-methyl-3-quinolinecarboxylic acid ethyl ester;

5,6,7,8-tetrahydro-2-methyl-8-(phenylmethylene)-3-quinolinecarboxylic acid ethyl ester;

5,6,7,8-tetrahydro-2-methyl-8-(phenylmethylene)-3-quinolinemethanol;

5,6,7,8-tetrahydro-8-(5-hydroxy-2-oxopentyl)-2-methyl-3-quinolinecarboxylic acid ethyl ester;

8-(2-furanylmethyl)-5,6,7,8-tetrahydro-2-methyl-3-quinolinecarboxylic acid ethyl ester;

5,6,7,8-tetrahydro-2-methyl-8-[(tetrahydro-2-furanyl)methyl]-3-quinolinecarboxylic acid ethyl ester;

3-[4-(acetyloxy)phenyl]-6',7'-dihydro-2-methyl-spiro[oxirane-2,8'-(5'H)-quinoline]-3-carboxylic acid ethyl ester and the 1' oxide thereof;

8-(2-furanylmethylene)-5,6,7,8-tetrahydro-2-methyl-3-quinolinecarboxylic acid ethyl ester;

5,6,7,8-tetrahydro-2-methyl-8-(2-oxopentyl)-3-quinolinecarboxylic acid ethyl ester;

5,6,7,8-tetrahydro-8-(2-hydroxypentyl)-2-methyl-3-quinolinecarboxylic acid ethyl ester;

5,6,7,8-tetrahydro-2-methyl-8-(phenylmethyl)-3-quinolinecarboxylic acid ethyl ester and hydrochloride salt thereof;

5,6,7,8-tetrahydro-2-methyl-8-(2-thienylmethylene)-3-quinolinecarboxylic acid ethyl ester; or 5,6,7,8-tetrahydro-8-(5-hydroxypentyl)-2-methyl-3-quinolinecarboxylic acid ethyl ester.

8. A compound according to claim 2 wherein the specific embodiment is 3-[5,6,7,8-tetrahydro-2-methyl-8-(phenylmethylene)-3-quinolinyl]-2-propenoic acid methyl ester.

9. A compound according to claim 1 wherein D is N→O.

10. A compound according to claim 9 wherein R$_2$ is CHO.

11. A compound according to claim 9 wherein the specific embodiment is the 1'-oxide of 3-[4-(acetyloxy)- phenyl]-6',7'-dihydro-2-methyl-spiro[oxirane-2,8'-(5'H)-quinoline]-3-carboxylic acid ethyl ester.

12. A method for the therapeutic or prophylactic treatment of allergy, asthma, chronic bronchitis, cystic fibrosis, psoriasis, or inflammatory bowel diseases comprising administration of an effective amount of a compound having the formula

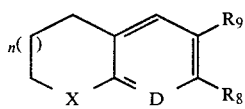   II wherein
D is N or N→O;
wherein
n is an integer 0 or 1;
wherein
$R_8$ is
  (a) hydrogen,
  (b) alkyl of from 1 to 4 carbons; inclusive,
  (c) cyclopropyl,

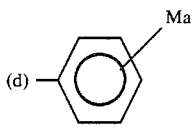   IX wherein a is an integer 0–2, inclusive, and wherein M is
  (i) hydrogen,
  (ii) halo,
  (iii) trifluoromethyl,
  (iv) S—$CH_3$,
  (v) phenyl,
  (vi) O—$CH_3$,
  (vii) OH,
  (viii) $NO_2$,
  (ix) $NR_3R_4$ wherein $R_3$ and $R_4$ are the same or different and are alkyl of from 1 to 4 carbons, inclusive, acyl, aroyl, hydrogen, or are taken together to form

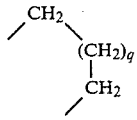   XI wherein q is an integer 2 or 3, except that when one of $R_3$ and $R_4$ is acyl or aroyl, the other of $R_3$ and $R_4$ cannot be acyl or aroyl,
  (x) $OCOCH_3$,
  (xi) $OCOC_6H_5$,
  (xii) O—Si$(CH_3)_2$C$(CH_3)_3$; and
wherein
$R_9$ is
  (a) hydrogen, or alkyl of 1 to 4 carbon atoms,
  (b) $COOR_5$ wherein $R_5$ is
    (i) hydrogen,
    (ii) alkyl of from one to four carbons, or
    (iii) a pharmaceutically acceptable cation,
  (c) $CH_2OH$,
  (d) CHO,
  (e) CH=CH—$(CH_2)_d R_6$ comprising the cis or trans isomer wherein d is an integer 0 through 3, inclusive, and $R_6$ is $CH_2OH$, $CH_2Cl$, or $CO_2R_5$ wherein $R_5$ is as defined above with the proviso that when $R_6$ is $CO_2R_5$ then d cannot be 0,
  (f) $CH_2CH_2(CH_2)_d R_6$ wherein d and $R_6$ are as defined above; and
wherein
X is

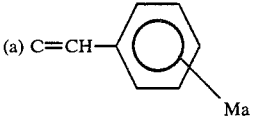   XII wherein M and a are as defined above,

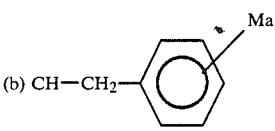   XIII wherein M and a are as defined above,

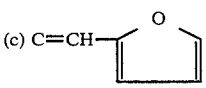   XIV

   XV

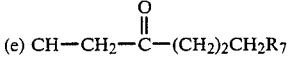

wherein $R_7$ is H, OH, Cl,

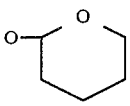   XVI or O—Si$(CH_3)_2$C$(CH_3)_3$,

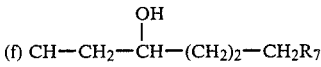

wherein $R_7$ is as defined above, or

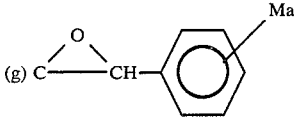   XVII wherein M and a are as defined above;

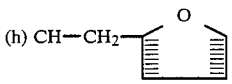   XVIII/XIX with the proviso that when $R_8$ and $R_9$ are both hydrogen and n is 0 then X cannot be

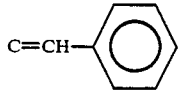   XII and with the proviso that when $R_8$ and $R_9$ are both hydrogen and n is 1 then M cannot be OC(=O) alkyl of from 1 to 4 carbons, inclusive; and pharmaceutically acceptable salts thereof.

13. A method according to claim 12 wherein D is N.

14. A method according to claim 13 wherein the compound is

8-[[4-(acetyloxy)phenyl]methylene]-5,6,7,8-tetrahydro-2-methyl-3-quinolinecarboxylic acid ethyl ester;

5,6,7,8-tetrahydro-2-methyl-8-(phenylmethylene)-3-quinolinecarboxylic acid ethyl ester;

5,6,7,8-tetrahydro-2-methyl-8-(phenylmethylene)-3-quinolinemethanol;

5,6,7,8-tetrahydro-8-(5-hydroxy-2-oxopentyl)-2-methyl-3-quinolinecarboxylic acid ethyl ester;

8-(2-furanylmethyl)-5,6,7,8-tetrahydro-2-methyl-3-quinolinecarboxylic acid ethyl ester;

5,6,7,8-tetrahydro-2-methyl-8-[(tetrahydro-2-furanyl)methyl]-3-quinolinecarboxylic acid ethyl ester;

3-[4-(acetyloxy)phenyl]-6',7'-dihydro-2-methylspiro[oxirane-2,8'-(5'H)-quinoline]-3-carboxylic acid ethyl ester and the 1' oxide thereof;

8-(2-furanylmethylene)-5,6,7,8-tetrahydro-2-methyl-3-quinolinecarboxylic acid ethyl ester;

5,6,7,8-tetrahydro-2-methyl-8-(2-oxopentyl)-3-quinolinecarboxylic acid ethyl ester;

5,6,7,8-tetrahydro-8-(2-hydroxypentyl)-2-methyl-3-quinolinecarboxylic acid ethyl ester;

5,6,7,8-tetrahydro-2-methyl-8-(2-thienylmethylene)-3-quinolinecarboxylic acid ethyl ester; or 5,6,7,8-tetrahydro-8-(5-hydroxypentyl)-2-methyl-3-quinolinecarboxylic acid ethyl ester;

5,6,7,8-tetrahydro-8-(phenylmethylene)quinoline;

6,7-dihydro-7-(2-thienylmethylene)-5H-1-pyrindine; and

4-[(5,6-dihydro-7H-pyrindin-7-ylidene)methyl]acetate.

15. A method according to claim 14 wherein the compound is the hydrogen chloride salt thereof.

16. A method according to claim 13 wherein the compound is 5,6,7,8-tetrahydro-2-methyl-8-(phenylmethyl)-3-quinolinecarboxylic acid ethyl ester.

17. A method according to claim 16 wherein the compound is the hydrogen chloride salt thereof.

18. A method according to claim 12 wherein D is N→O.

* * * * *

UNITED STATES PATENT OFFICE
CERTIFICATE OF CORRECTION

Patent No. 4,576,949   Dated 18 March 1986

Inventor(s) Herman W. Smith

It is certified that error appears in the above-identified patent and that said Letters Patent are hereby corrected as shown below:

Columns 5 and 6 (Table II): "N XVII" should read --N XVIII--.
Columns 5 and 6 (Table II) under 1.0 and 10 µg:   121 50 and ___ ___"
should read -- 121 50 and 95 101--.
Column 9, line 38:   "137" should read --1.37--.
Column 10, line 50:   "(S,C_3)" should read --(S,CH_3)--.
Column 11, line 11:   "(68" should read --($\varepsilon$--.
Column 11, line 61:   "67" should read --$\delta$--.
Column 14, line 33:   "CH=O" should read --CH-O--.
Column 25, (claim 12) line 2:   "XII" should read --IX--.

Signed and Sealed this

Twenty-eighth Day of October, 1986

[SEAL]

Attest:

DONALD J. QUIGG

Attesting Officer   Commissioner of Patents and Trademarks